(12) United States Patent
Maschino et al.

(10) Patent No.: US 12,076,219 B2
(45) Date of Patent: Sep. 3, 2024

(54) FILMS AND LAMINATES FOR ABSORBENT ARTICLES

(71) Applicant: FITESA FILM PRODUCTS LLC, Simpsonville, SC (US)

(72) Inventors: Andrew D. Maschino, Paris, IL (US); Brian C. Loomis, Terre Haute, IN (US); Paul Eugene Thomas, Terre Haute, IN (US)

(73) Assignee: FITESA FILM PRODUCTS LLC, Simpsonville, SC (US)

( * ) Notice: Subject to any disclaimer, the term of this patent is extended or adjusted under 35 U.S.C. 154(b) by 895 days.

(21) Appl. No.: 17/095,309

(22) Filed: Nov. 11, 2020

(65) Prior Publication Data

US 2021/0145653 A1    May 20, 2021

Related U.S. Application Data

(60) Provisional application No. 62/976,911, filed on Feb. 14, 2020, provisional application No. 62/935,468, filed on Nov. 14, 2019.

(51) Int. Cl.
*A61F 13/15* (2006.01)
*A61F 13/51* (2006.01)
*A61F 13/511* (2006.01)

(52) U.S. Cl.
CPC ........ *A61F 13/15699* (2013.01); *A61F 13/51* (2013.01); *A61F 2013/15552* (2013.01);
(Continued)

(58) Field of Classification Search
CPC ................ A61F 13/15699; A61F 13/51; A61F 2013/15552; A61F 2013/15926; A61F 2013/51078; A61F 2013/51165
See application file for complete search history.

(56) References Cited

U.S. PATENT DOCUMENTS

| 7,198,836 B2 | 4/2007 | Thomas |
| 8,182,728 B2 | 5/2012 | Cree et al. |

(Continued)

FOREIGN PATENT DOCUMENTS

| CN | 105411754 A | 3/2016 |
| CN | 109477269 A | 3/2019 |

(Continued)

OTHER PUBLICATIONS

International Search Report and Written Opinion dated Mar. 11, 2021, for International Patent Application No. PCT/US2020/059993.

(Continued)

*Primary Examiner* — Jacqueline F Stephens
(74) *Attorney, Agent, or Firm* — Karceski IP Law, PLLC

(57) ABSTRACT

A film for use in an absorbent article includes a first side and a second side opposite the first side, and a plurality of apertured protuberances arranged in a pattern having 60 to 120 protuberances per linear inch in at least one direction. Each of the protuberances includes a continuous sidewall extending from the first side. The second side has a plurality of apertures aligned with the plurality of apertured protuberances and land areas in between the apertures. The film has a melt index of at least about 8 g/10 min, and an air permeability of at least about 80 m³/m²/min.

23 Claims, 14 Drawing Sheets

(52) U.S. Cl.
CPC ............... *A61F 2013/15926* (2013.01); *A61F 2013/51078* (2013.01); *A61F 2013/51165* (2013.01)

(56) References Cited

U.S. PATENT DOCUMENTS

| | | | |
|---|---|---|---|
| 10,258,517 | B1 | 4/2019 | Maschino et al. |
| 2005/0054998 | A1 | 3/2005 | Poccia et al. |
| 2005/0133151 | A1 | 6/2005 | Pacheco et al. |
| 2016/0106602 | A1* | 4/2016 | Seyler .................. A61F 13/512 604/372 |
| 2017/0165880 | A1 | 6/2017 | Thomas |
| 2018/0256414 | A1 | 9/2018 | Maschino et al. |
| 2019/0270224 | A1 | 9/2019 | Thomas |

FOREIGN PATENT DOCUMENTS

| | | |
|---|---|---|
| JP | H06304203 A | 11/1994 |
| JP | H07501244 A | 2/1995 |
| JP | 2005312526 A | 11/2005 |
| KR | 20170071562 A | 6/2017 |

OTHER PUBLICATIONS

Japanese Office Action dated May 9, 2023, for Japanese Patent Application No. 2022-527182.
International Preliminary Report on Patentability dated May 27, 2022, for International Patent Application No. PCT/US2020/059993.
Chinese Office Action dated Aug. 24, 2022, for Chinese Patent Application No. 202080087019.8.
Chinese Office Action dated Mar. 28, 2023, for Chinese Patent Application No. 202080087019.8.
Indian Office Action dated Oct. 7, 2022, for Indian Patent Application No. 202217027923.
Chinese Office Action dated Aug. 3, 2023, for Chinese Patent Application No. 202080087019.8.
Japanese Office Action dated Nov. 21, 2023, for Japanese Patent Application No. 2022-527182.
Korean Office Action dated Nov. 7, 2023, for Korean Patent Application No. 10-2022-7019422.

* cited by examiner

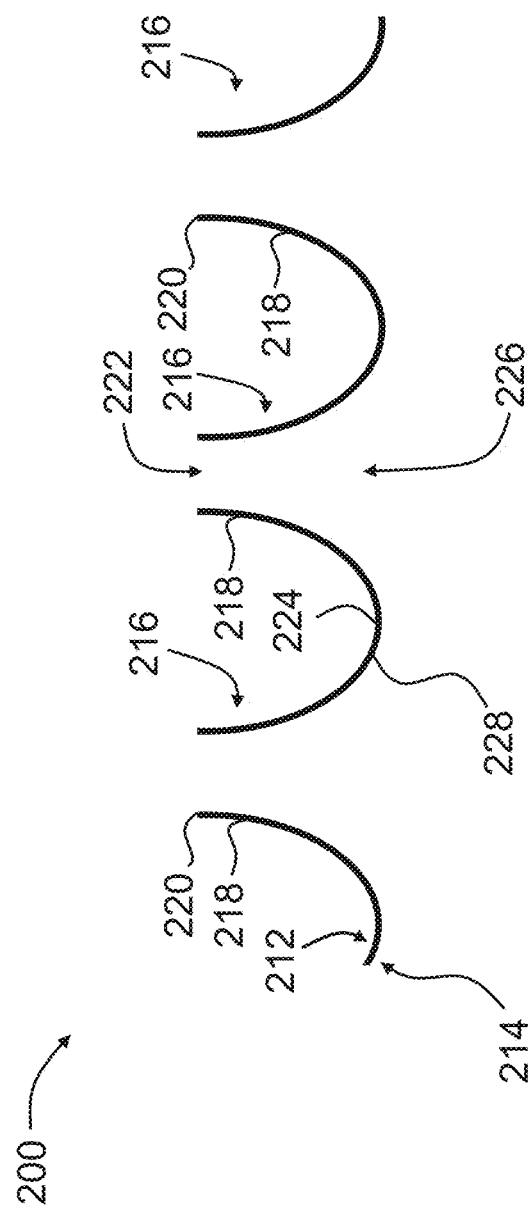

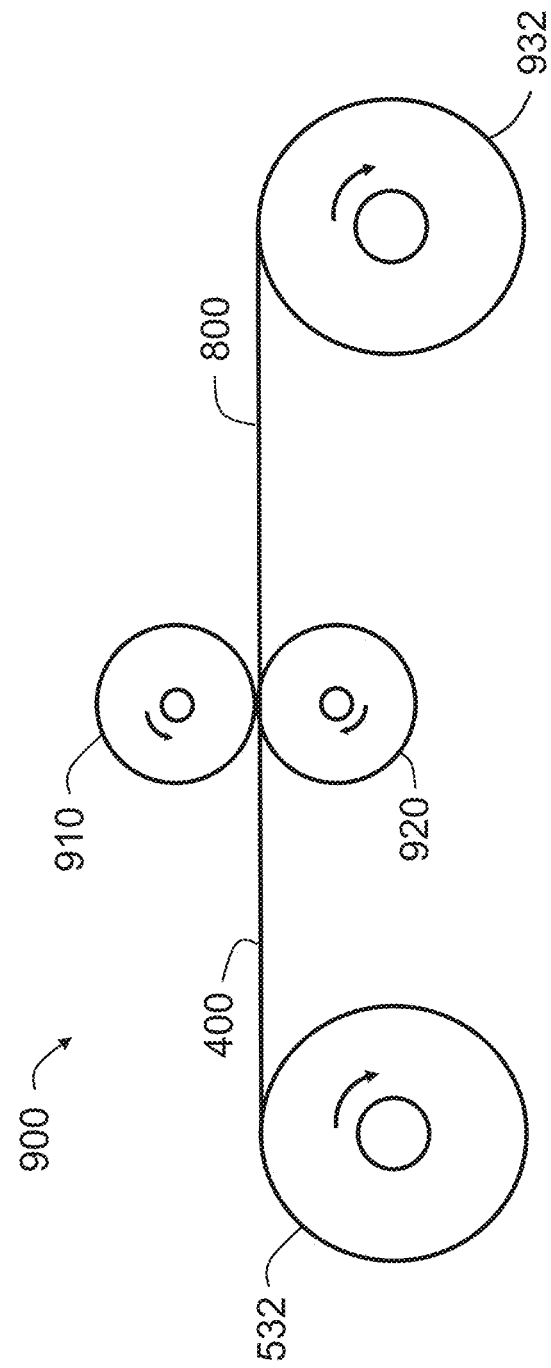

FILMS AND LAMINATES FOR ABSORBENT ARTICLES

CROSS-REFERENCE TO RELATED APPLICATIONS

This application claims the benefit of priority from U.S. Provisional Patent Application Ser. No. 62/935,468, filed Nov. 14, 2019, and U.S. Provisional Patent Application Ser. No. 62/976,911, filed Feb. 14, 2020, the contents of both of which are hereby incorporated by reference in their entireties.

FIELD

The present invention is directed to films and laminates that may be used in absorbent articles, as well as absorbent articles that include such films and laminates.

BACKGROUND

A variety of well-known absorbent articles are configured to absorb body fluids. Examples of such absorbent articles include, but are not limited to, feminine hygiene products, such as sanitary napkins or pads, baby diapers, adult incontinence products, and bandages. A typical absorbent article is generally constructed with a fluid permeable user-facing topsheet, which may be an apertured polymer film or a nonwoven web or a film/nonwoven laminate, an absorbent core, and a fluid impermeable garment or outwardly-facing backsheet, which may be a solid polymer film, for example.

In general, topsheets that are made from polymer films have better performance characteristics when used in the end-product as compared to topsheets that are made from nonwoven materials. However, a topsheet made from a polymer film may have a visual appearance that is higher in gloss and therefore may be more "plastic-looking" than a non-woven topsheet, and a polymer film topsheet may feel more "sticky" or "tacky" and less soft to the wearer than a nonwoven topsheet.

It is desirable to create a topsheet that delivers extraordinary softness to the user, assures performance at least comparable to traditional films.

SUMMARY

According to an aspect of the invention, there is provided a film for use in an absorbent article. The film has a first side and a second side opposite the first side, and a plurality of apertured protuberances arranged in a pattern having 60 to 120 protuberances per linear inch in at least one direction. Each of the protuberances includes a continuous sidewall extending from the first side. The second side has a plurality of apertures aligned with the plurality of apertured protuberances and land areas in between the apertures. The film has a melt index of at least about 8 g/10 minutes, and an air permeability of at least about 80 meter$^3$/meter$^2$/minute.

In an embodiment, the film has a basis weight between about 10 gsm and about 30 gsm.

According to an aspect of the invention, there is provided a laminate for use in an absorbent article. The laminate includes a film layer having a first side and a second side opposite the first side. The film layer includes a plurality of apertured protuberances arranged in a pattern having 60 to 120 protuberances per linear inch in at least one direction. Each of the protuberances includes a continuous sidewall extending from the first side. The second side has a plurality of apertures aligned with the plurality of apertured protuberances and land areas in between the apertures. The film layer has a melt index of at least about 8 g/10 minutes and an air permeability of at least about 80 meter$^3$/meter$^2$/minute. The laminate includes a nonwoven layer laminated to the second side of the film layer. The nonwoven layer includes a plurality of fibers attached to the formed film at the land areas of the film layer.

In an embodiment, the nonwoven layer has a basis weight of between about 8 gsm and about 60 gsm.

In an embodiment, the nonwoven layer includes a spunbond nonwoven.

In an embodiment, the nonwoven layer includes a carded nonwoven.

In an embodiment, the nonwoven layer comprises a spunlace nonwoven.

In an embodiment, the film layer has a basis weight of between about 4 gsm and about 20 gsm.

In an embodiment, the laminate includes a plurality of apertures extending through the film layer and the nonwoven layer. The plurality of apertures has a pattern with a mesh count between about 3 and about 40 apertures per linear inch in at least one direction.

In an embodiment, the laminate has an embossed pattern.

In an embodiment, the embossed pattern includes a plurality of narrow ridges. In an embodiment, the plurality of narrow ridges includes narrow, wavy ridges.

According to an aspect of the invention, there is provided a laminate for use in an absorbent article. The laminate includes a first film layer having a first side and a second side opposite the first side. The first film layer includes a first plurality of apertured protuberances arranged in a pattern having 60 to 120 protuberances per linear inch in at least one direction. Each of the first plurality of apertured protuberances includes a continuous sidewall extending from the first side. The second side has a first plurality of apertures aligned with the first plurality of apertured protuberances and first land areas in between each of the first plurality of apertures. The first film layer has a melt index of at least about 8 g/10 min and an air permeability of at least about 80 m$^3$/m$^2$/min. The laminate also includes a second film layer having a first side and a second side opposite the first side. The second film layer includes a second plurality of apertured protuberances arranged in a pattern having 3 to 40 protuberances per linear inch in at least one direction. Each of the second plurality of apertured protuberances includes a continuous sidewall extending from the first side. The second side has a second plurality of apertures aligned with the second plurality of apertured protuberances and second land areas in between each of the second plurality of apertures. The second side of the first film layer is attached to the second side of the second film layer.

In an embodiment, the first film layer has a basis weight of between about 4 gsm and about 20 gsm.

In an embodiment, the second film layer has a basis weight of between about 10 gsm and about 40 gsm.

According to an aspect of the invention, there is a provided a method for making a material for an absorbent article. The method includes vacuum forming a plurality of apertured protuberances into a polymer web to create a first film using a forming structure comprising a pattern of 60 to 120 apertures per linear inch in at least one direction. The first film has a melt index of at least about 8 g/10 minutes and an air porosity of at least about 80 meter$^3$/meter$^2$/minute.

In an embodiment, the method includes laminating a nonwoven to the first film to form a film/nonwoven laminate.

In an embodiment, the method includes aperturing the film/nonwoven laminate to create a plurality of apertures having a mesh count between about 3 to about 40 apertures per linear inch in at least one direction.

In an embodiment, the method includes embossing the film/nonwoven laminate to create an embossed pattern in the film/nonwoven laminate.

In an embodiment, the embossed patterned includes a plurality of narrow ridges. In an embodiment, the plurality of narrow ridges includes narrow, wavy ridges.

In an embodiment, the method includes laminating a second film to the first film to form a film/film laminate.

In an embodiment, the second film includes a plurality of apertures arranged in a pattern of 3 to 40 apertures per linear inch in at least one direction.

These and other aspects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

The components of the following figures are illustrated to emphasize the general principles of the present disclosure and are not necessarily drawn to scale. Reference characters designating corresponding components are repeated as necessary throughout the figures for the sake of consistency and clarity.

FIG. 2B is a schematic enlarged cross-section taken along line 2B-2B in FIG. 2A;

FIG. 9 is a schematic representation of an apparatus for manufacturing the embossed film/nonwoven laminate of FIGS. 8A and 8B;

DETAILED DESCRIPTION

Figure 1:
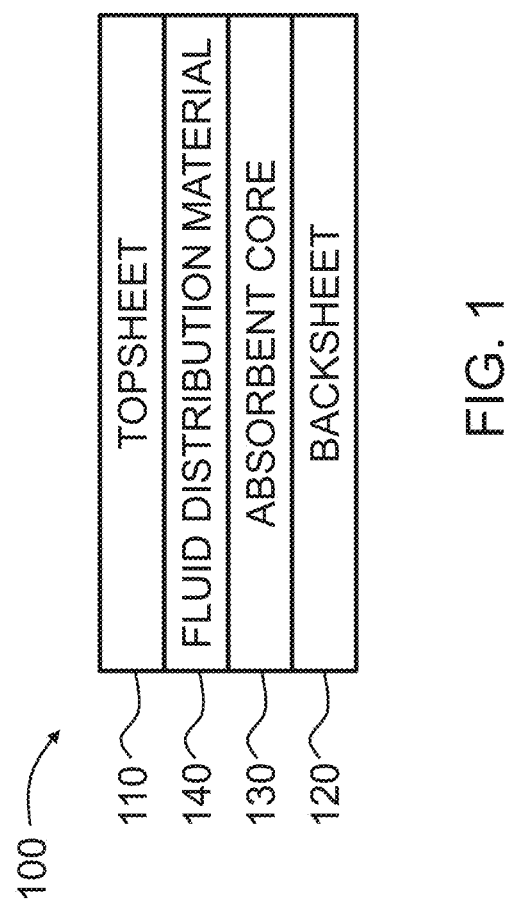
FIG. 1 is a schematic representation of an absorbent article in accordance with embodiments of the invention.

As used herein, the expression "absorbent articles" denote articles that absorb and contain body fluids and other body exudates. More specifically, an absorbent article/absorptive device includes garments that are placed against or in proximity to the body of a wearer to absorb and contain the various exudates discharged from a body. Non-limiting examples of absorbent articles include, but are not limited to feminine hygiene products, baby diapers, adult incontinence products, and bandages.

Throughout this description, the term "web" refers to a material capable of being wound into a roll. Webs can be film webs, nonwoven webs, laminate webs, apertured laminate webs, etc. The face of a web refers to one of its two dimensional surfaces, as opposed to one of its edges.

The term "laminate web" or "laminate" refers to a web that comprises two or more separate webs that are attached to each other in a face to face relationship. The two or more separate webs may include one or more film webs and/or nonwoven webs. The attachment may be at particular spot locations across the component webs, or the attachment may be continuous across the component webs.

The term "film" or "polymer film" in this description refers to a web made by extruding a molten curtain or sheet of thermoplastic polymeric material by a cast or blown extrusion process and then cooling the sheet to form a solid polymeric web. Films can be monolayer films, coextruded films, coated films, and/or composite films.

Throughout this description, the expression "apertured films" and "apertured laminates" denote films and laminates that have a plurality of apertures that extend from a first surface of the film or laminate to a second, opposing surface of the film or laminate.

A "two-dimensional apertured film" is a film in which no three-dimensional structure exists in the apertures, which then connect the second surface of a flat film to the first surface of the film.

A "formed film" or a "three-dimensional film" is a film with protuberances, protrusions, or extended cells extending from at least one side thereof, and an "apertured formed film" or a "three-dimensional apertured film" is a film in which a three-dimensional structure exists in the apertures (e.g., the apertures have a depth that is thicker than the thickness of the film), or the protuberances or protrusions or extended cells have apertures therethrough.

The term "protuberance" as used herein refers to a three-dimensional member comprising an apertured base portion located in the plane of the first surface of the film and a sidewall portion extending generally in the direction of the second surface of the film. Each base portion has an associated sidewall portion. Sidewall portions terminate in "distal ends" located in the plane of the second surface of the film. The distal ends of the protuberances may be apertured or unapertured.

"Apertured protuberance" as used herein refers to a protuberance that has an aperture at its base portion or proximal end in the plane of the first surface, as well as its distal or protubered end. The apertures in the base portions of the protuberances, also called "primary apertures," may be in the shape of polygons, for example squares, hexagons, pentagons, ellipses, circles, ovals, or slots, in a regulated or random pattern. In an embodiment, the apertures may be in the shape of a boat, as described in, for example, U.S. Pat. No. 7,198,836, which is incorporated herein by reference.

The apertured distal or protubered ends are called "secondary apertures," and may be in the shape of polygons, e.g., squares, hexagons, pentagons, ellipses, circles, ovals, slots, or boats. The sidewall portion of the apertured protuberance extends from the primary aperture to the secondary aperture.

The term "nonwoven" means a web comprising a plurality of fibers. The fibers may be bonded to each other or may be unbonded. The fibers may be staple fibers or continuous fibers or filaments. The fibers may comprise a single material or may comprise a multitude of materials, either as a combination of different fibers or as a combination of similar fibers with each comprised of different materials.

As used herein, "nonwoven web" is used in its generic sense to define a generally planar structure that is relatively flat, flexible and porous, and includes staple fibers or continuous fibers or filaments. The nonwoven web may be the product of any process for forming the same, such as nonwoven spunbond and melt blown nonwoven webs. The nonwoven web may include a composite or combination of webs. The nonwoven web may comprise any polymeric material from which a fiber can be produced and/or may comprise cotton or other natural fibers. In an embodiment, the nonwoven web may be a spunbond material, made of polypropylene fiber. Fibers that comprise different polymers may also be blended. In an embodiment, the fibers may be so-called bi-component ("bi-co") fibers that comprise a core of one material and a sheath of another material.

The term "forming structure" or "screen" as used herein refers to a three-dimensional molding apparatus that comprises indentations used to form protuberances, and/or apertures in films, or protuberances in nonwoven webs. In an embodiment, forming structures comprise tubular members, having a width and a diameter. In alternative embodiments, forming structures may comprise belts having a width and a length. The transverse direction is the direction parallel to the width of the forming structure. The machine direction is the direction parallel to the direction of rotation of the forming structure, and is perpendicular to the transverse direction.

The term "air permeability" as used herein is a measure of air flow through a material using a Textest FX3300 Air Permeability Tester in accordance with ASTM D737. The units are reported in cubic meters per square meter per minute ($m^3/m^2/min$).

The term "melt index" as used herein is a measure of material flow when the material is heated to 190° C. and subjected to a 2.16 kg mass in accordance with ASTM D1238. The units are grams per 10 minutes (g/10 min).

Various embodiments of the present invention will now be described. The discussion of any one embodiment is not intended to limit the scope of the present invention. To the contrary, aspects of the embodiments are intended to emphasize the breadth of the invention, whether encompassed by the claims or not. Furthermore, any and all variations of the embodiments, now known or developed in the future, also are intended to fall within the scope of the invention.

FIG. 1 schematically illustrates an absorbent article 100 in accordance with embodiments of the invention. As illustrated, the absorbent article 100 includes a topsheet 110, a backsheet 120, and an absorbent core 130 positioned in between the topsheet 110 and the backsheet 120. The absorbent article 100 may also include a fluid distribution material 140 positioned in between the topsheet 110 and the absorbent core 130.

The topsheet 110, which may be in the form of a two-dimensional or three-dimensional apertured film, a nonwoven web, or a laminate of an apertured film and a nonwoven web, is permeable to fluids and is configured to face the user wearing the absorbent article 100 and contact the user's skin. The topsheet 110 receives insults of fluid from the user, and the fluid passes through the topsheet 110 to the fluid distribution material 140. The fluid distribution material 140, if used, is also permeable and is configured to receive the fluid from the topsheet 110 and distribute the fluid to the absorbent core 130. The absorbent core 130, which includes absorbent materials, receives the fluid from the fluid distribution material 140 and stores the fluid until the absorbent article 100 is discarded. The backsheet 120, which is impermeable to liquid and may be in the form of a polymer film or laminate of a polymer film and nonwoven web, prevents liquid and other body exudates from leaking out of the bottom side of the absorbent core 130. The backsheet 120 may be breathable so that air, but not liquid, may pass through.

Figure 2A:
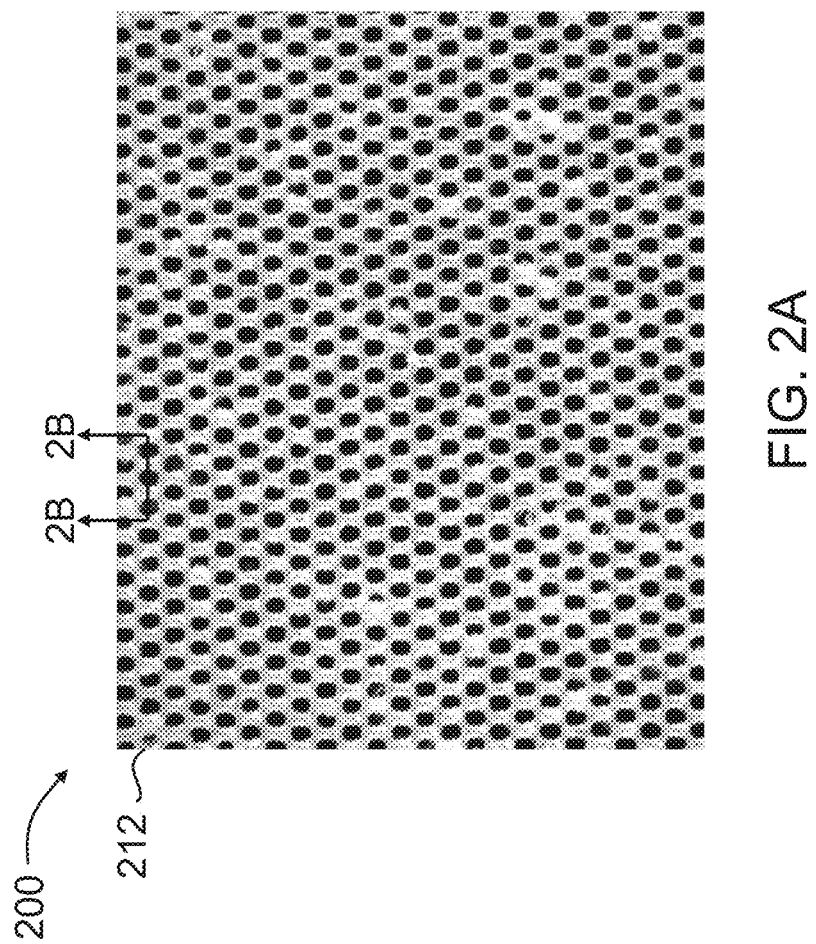
FIG. 2A is a microphotograph of a top view of an embodiment of a film that may be used as part of the absorbent article of FIG. 1.

FIG. 2A is a microphotograph of a portion of a film 200 according to an embodiment of the invention, which may be used as the topsheet material 110 of FIG. 1, and FIG. 2B schematically illustrates a cross-section of the topsheet material 200 taken along lines 2B-2B of FIG. 2A. As illustrated, the film 200 a first side 212 and a second side 214 that is opposite the first side 212. The film 200 includes a plurality of apertured protuberances 216. Each of the apertured protuberances 216 includes a continuous sidewall 218 extending from the first side 212 of the film 200 to a distal end 220 that includes a secondary aperture 222, as illustrated. The first side 212 of the film 200 also includes land areas 224 in between the apertured protuberances 216.

The second side 214 of the film 200 has a plurality of primary apertures 226 aligned with the plurality of protuberances 216. As such, the primary apertures 226 in the second side 214 of the film 200 are also considered to be proximal apertures 226 of the apertured protuberances 216, while the secondary apertures 222 at the distal ends 220 of the apertured protuberances 216 may also be considered to be distal apertures 222 of the apertured protuberances 216. The second side 214 of the film 200 also includes land areas 228 in between the proximal apertures 226.

In an embodiment, the apertured protuberances 216 may be arranged in a pattern having about 60 to about 120 protuberances per linear inch or "mesh," i.e., about 60 mesh to about 120 mesh in at least one direction. The pattern may be a hexagonal pattern, a square pattern, a staggered pattern, or any other type of pattern or design. In an embodiment, the proximal apertures 226 may be hexagonal in shape and have approximately the same size.

The polymer of the film 200 may include one or more polyolefins, including but not limited to polyethylene, ultra-low density polyethylene, low density polyethylene, linear low density polyethylene, linear medium density polyethylene, high density polyethylene, polypropylene, ethylene-vinyl acetates, metallocene, as well as other polymers, such as bio-based polymers that are produced from plants, including but not limited to sugarcane, or polylactic acid ("PLA"). Other polymers also include, but are not limited to, elastomeric polymers, including but not limited to polypropylene based elastomers, ethylene based elastomers, copolyester based elastomers, olefin block copolymers, styrenic block copolymers and the like, or combinations thereof. Additives, such as surfactants, fillers, colorants, opacifying agents and/or other additives known in the art may also be used in the film 200.

In an embodiment, the film 200 may have a basis weight of between about 10 grams per square meter ("gsm") and about 30 gsm. In an embodiment, the film 200 may have a basis weight of between about 15 gsm and about 25 gsm.

Figure 3:
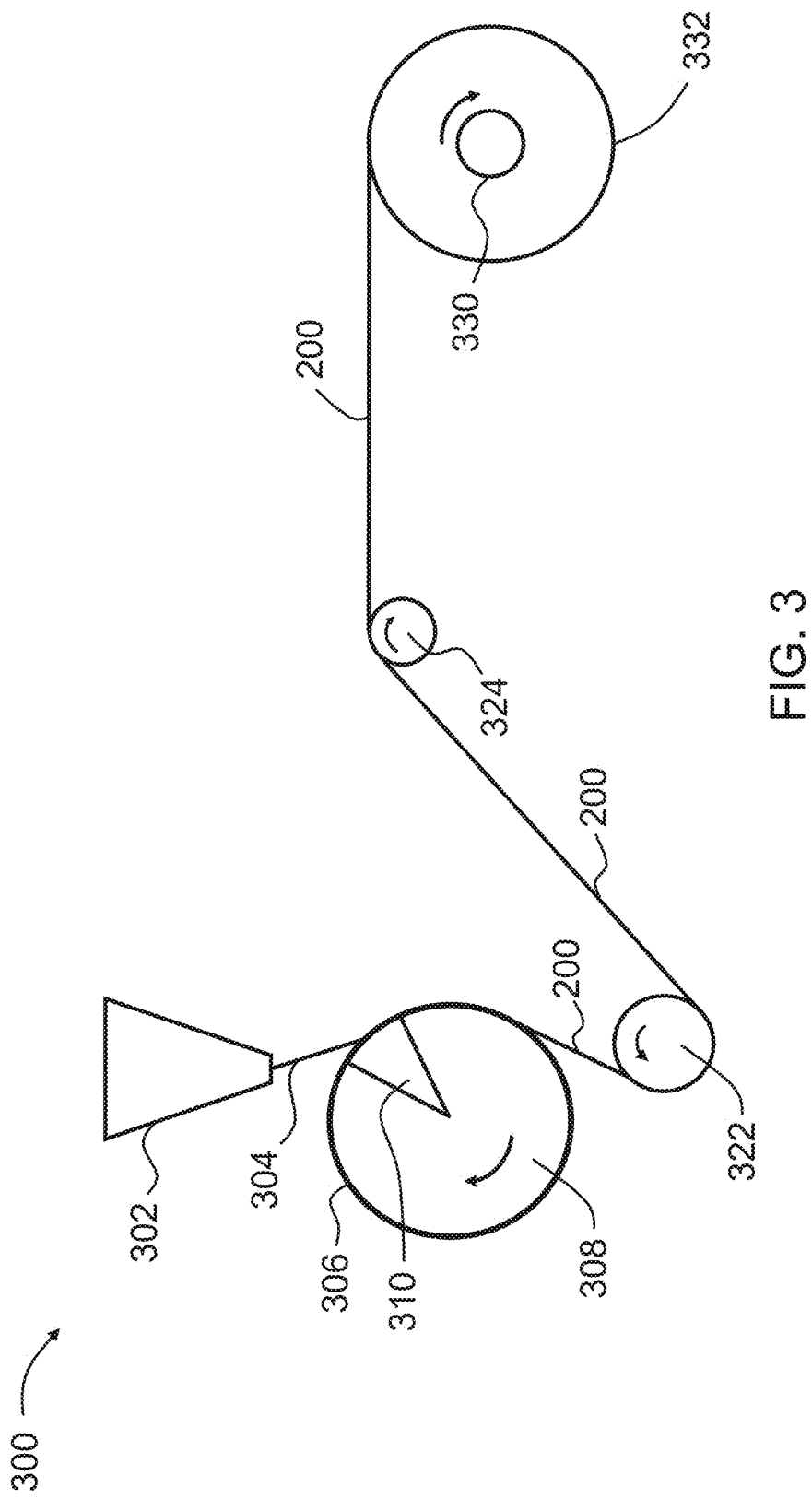
FIG. 3 is a schematic representation of an apparatus for manufacturing the film of FIGS. 2A and 2B in accordance with embodiments of the invention.

FIG. 3 schematically illustrates an apparatus 300 that may be used to manufacture the film 200 of embodiments of the invention described herein. As illustrated, an extrusion die 302 extrudes polymer melt curtain 304 onto a forming structure 306 that rotates about a cylinder 308 that has a vacuum slot 310 through which a vacuum is pulled. The polymer melt curtain 304 may include, for example, one or more polyolefin materials and a surfactant, as well as one or more additives, such as a colorant.

As the polymer web (which solidifies to form, for example, the film 200 of FIGS. 2A and 2B) is apertured, air flow is initiated through the apertured protuberances (e.g., 216) which cools and solidifies the apertured protuberances (e.g., 216). The polymer web is also cooled by the forming structure 306. The resulting vacuum formed film 200 is pulled off of forming structure 306 by a peel roller 322 and travels to one or more subsequent rollers 324 until it may be wound by a winder 330 into a roll 332. Additional rollers and/or other pieces of equipment may be used in the apparatus 300. The illustrated embodiment is not intended to be limiting in any way.

EXAMPLES

A series of films 200 was created using the apparatus 300 described above. The forming structure 306 had a pattern of apertures arranged with 100 apertures per linear inch in at least one direction (i.e. 100 mesh). Different blends were used to create films having different melt index values, but with the same target basis weight of 18 grams per square meter (gsm). The Comparative Example was a typical blend of polyethylenes and masterbatches that included a surfactant and white pigment that is used to make vacuum formed films. The resulting film formed for the Comparative Example was measured to have an air permeability of 3.0 $m^3/m^2/min$, which indicates that very few apertures were created using the 100 mesh forming structure. It was difficult to measure the melt index of the actual blend of materials, so the melt index of the resulting film was measured instead, which was found to be 4.0 g/10 min.

Without being bound by theory, it was postulated that increasing the melt index of the blend of materials used may provide better flow of the melt curtain into the apertures of the 100 mesh forming structure 306 and result in more apertures being formed in the film and therefore result in higher air permeability. To increase the melt index of the blend for the film 200, three different series of blends (Examples 1-5; Examples 6-8; Examples 9-11) were investigated, with each blend including the same masterbatches that included a surfactant and white pigment that is used to make the Comparative Example. Each film was measured for film melt index and air permeability. A summary of the test results is listed in Table I below:

TABLE I

Film Melt Index and Porosity

| Example | Film Melt Index (g/10 min) | Porosity ($m^3/m^2/min$) |
|---|---|---|
| Comparative | 4.0 | 3.0 |
| 1 | 5.0 | 18.2 |
| 2 | 6.5 | 44.2 |
| 3 | 8.2 | 81.2 |
| 4 | 8.3 | 142.6 |
| 5 | 13.2 | 204.4 |
| 6 | 13.4 | 133.4 |
| 7 | 15.6 | 171.4 |
| 8 | 19.2 | 150.8 |
| 9 | 12.9 | 171.8 |
| 10 | 13.4 | 198.0 |
| 11 | 14.0 | 198.2 |

The results indicate that for each series of blends, increasing the melt index of the film by increasing the melt index of the blend resulted in films with increased air permeability, which improves the fluid handling properties and softness of the films.

Film samples of Examples 3, 5 and 7, as well as the Comparative Example were used as topsheets, with the apertured protuberances 416 facing outward, and assembled into feminine hygiene pads for a panel test to determine relative softness of the samples. A total of ten panelists ranked each set of four sample in order of perceived softness, with 1 being least soft and 4 being most soft. A summary of the results is listed in Table II below:

TABLE II

Panel Results for Softness

| Example | Film Melt Index (g/10 min) | Average Ranking |
|---|---|---|
| Comparative | 4.0 | 1.0 |
| 3 | 8.2 | 2.8 |
| 5 | 13.2 | 2.7 |
| 7 | 15.6 | 3.5 |

The panel results indicate that the Comparative Example, which had the lowest film melt index, was ranked by each of the ten panelists as least soft, and Example 7, which had the highest film melt index was ranked, on average, the softest.

Figure 4B:
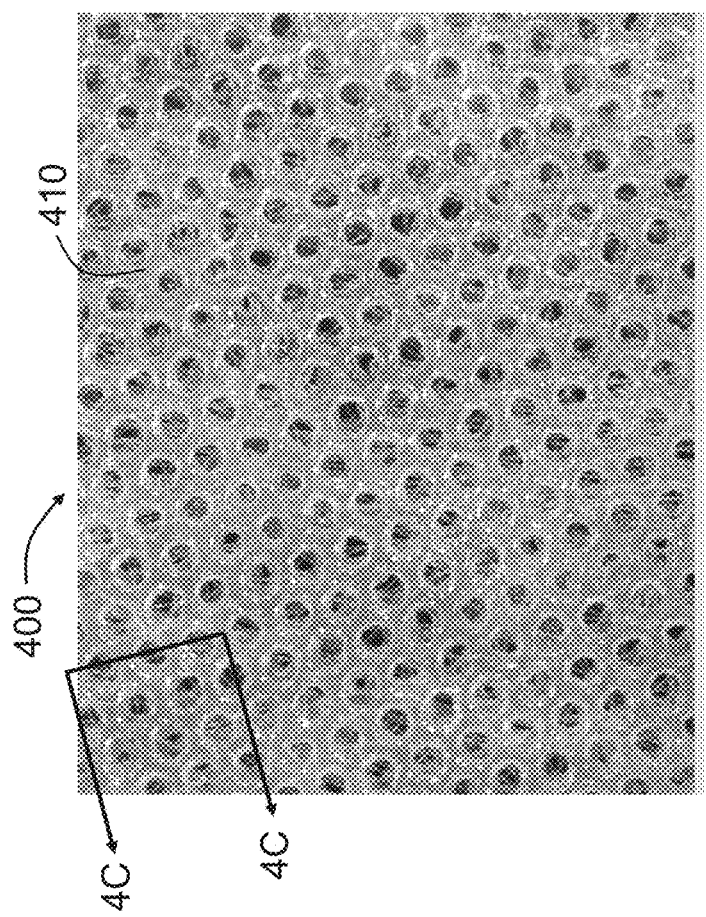
FIG. 4B is an enlarged microphotograph of an opposite side of the film/nonwoven laminate of FIG. 4A.
Figure 4A:
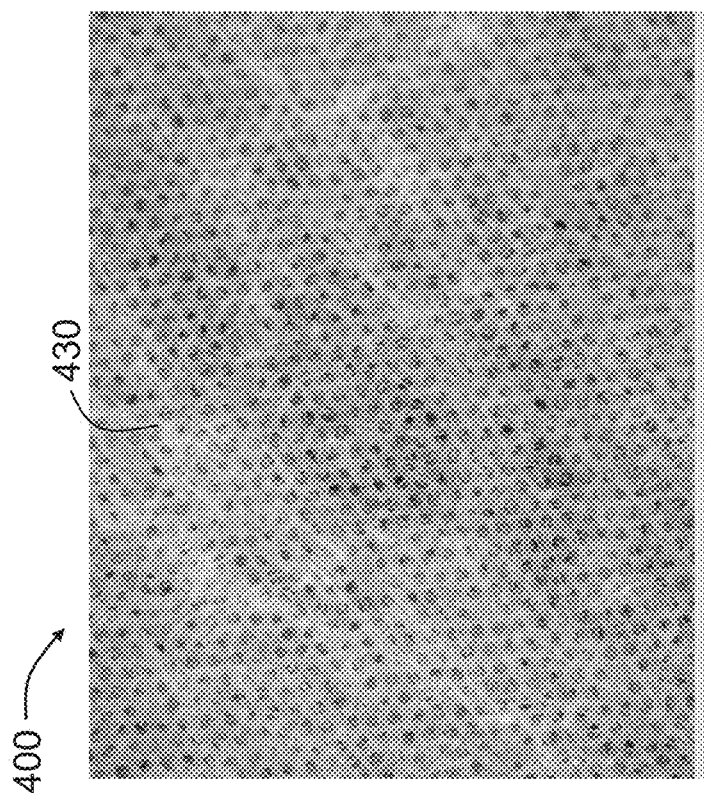
FIG. 4A is a microphotograph of one side of an embodiment of a film/nonwoven laminate that may be used as part of the absorbent article of FIG. 1.

FIG. 4A is a microphotograph of a portion of one side of a film/nonwoven laminate 400 in accordance with an embodiment of the invention, which may be used as the topsheet 110 for the absorbent article of FIG. 1, with a nonwoven layer 430 of the film/nonwoven laminate 400 on top. FIG. 4B is an enlarged microphotograph of a portion of the film/nonwoven laminate 400 with a film layer 410 on top, and FIG. 4C is a schematic illustration of a cross section of the film/nonwoven laminate 400 taken along lines 4C-4C.

Figure 4C:
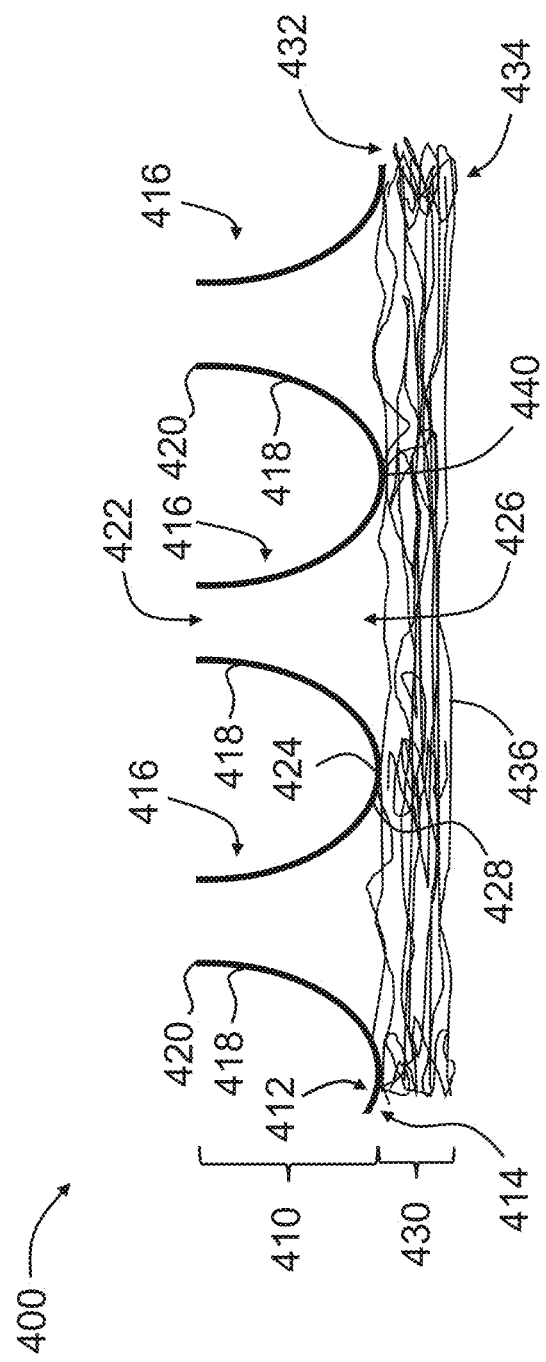
FIG. 4C is a schematic enlarged cross-section taken along line 4C-4C in FIG. 4B.

As illustrated in FIG. 4C, the film layer 410 has a first side 412 and a second side 414 that is opposite the first side 412. The film layer 410 includes a plurality of apertured protuberances 416. Each of the apertured protuberances 416 includes a continuous sidewall 418 extending from the first side 412 of the film layer 410 to a distal end 420 that includes a secondary aperture 422, as illustrated. The first side 412 of the film layer 410 also includes land areas 424 in between the apertured protuberances 416.

The second side 414 of the film layer 410 has a plurality of primary apertures 426 aligned with the plurality of protuberances 416. As such, the primary apertures 426 in the second side 414 of the film layer 410 are also considered to be proximal apertures 426 of the apertured protuberances 416, while the secondary apertures 422 at the distal ends 420 of the apertured protuberances 416 may also be considered to be distal apertures 422 of the apertured protuberances 416. The second side 414 of the film layer 410 also includes land areas 428 in between the proximal apertures 426. The film layer 410 may include one or more of the polymers listed about with respect to the film 200, and may have a basis weight between about 4 gsm and about 20 gsm.

In an embodiment, the apertured protuberances 416 may be arranged in a pattern having about 60 to about 120 protuberances per linear inch or "mesh," i.e., about 60 mesh to about 120 mesh in at least one direction. The pattern may be a hexagonal pattern, a square pattern, a staggered pattern, or any other type of pattern or design. In an embodiment, the proximal apertures 426 may be hexagonal in shape and have approximately the same size.

The nonwoven layer 430 has a first side 432 and a second side 434 opposite the first side 432. In the illustrated embodiment, the first side 432 of the nonwoven layer 430 contacts the second side 414 of the film layer 410. The nonwoven layer 430 includes a plurality of fibers 436.

Nonwoven webs that may be used for the nonwoven layer 430 may be formed from many processes, including but not limited to spunbonding processes, melt-blowing processes, hydroentangling processes, spunlacing processes, air-laying, and bonded carded web processes, or combinations thereof, as are known in the nonwoven art. In an embodiment, the nonwoven layer 430 may be a spunbonded nonwoven web. In an embodiment, the fibers 436 in the nonwoven layer 430 may be polypropylene fibers. In an embodiment, the nonwoven layer 430 may include natural fibers, such as cotton. In an embodiment, the nonwoven layer 430 may include bio-based fibers that include polymers that are produced from plants, including but not limited to sugarcane, or polylactic acid ("PLA"). The nonwoven layer 430 may have a basis weight of between about 8 gsm and about 60 gsm.

The film layer 410 is attached to the nonwoven layer 430 at bond sites 440 where the first side 432 of the nonwoven layer 430 contacts the land areas 428 of the second surface 414 of the film layer 410. In an embodiment, the fibers 436 at the bond sites 440 are embedded into the land areas 428 of the film layer 410, which may be accomplished by a vacuum formed lamination process, as described in further detail below. The bond sites 440 are contemplated to be distributed in a pattern, commensurate with some or all of the land areas 428.

Figure 5:
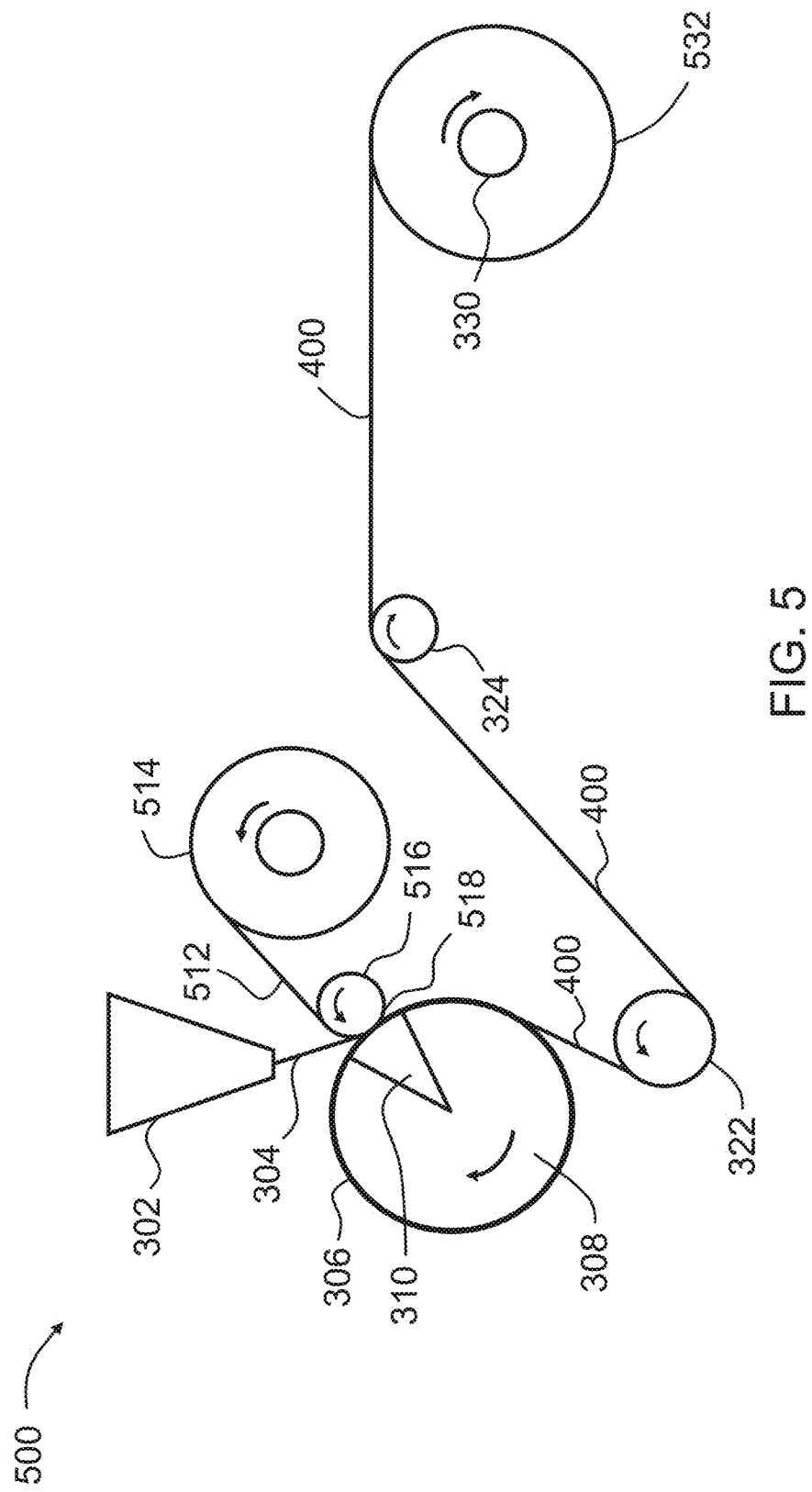
FIG. 5 is a schematic representation of an apparatus for manufacturing the film/nonwoven laminate of FIGS. 4A, 4B and 4C in accordance with embodiments of the invention.

FIG. 5 illustrates an embodiment of an apparatus 500 that may be used to manufacture the film/nonwoven laminate 400 of FIGS. 4A-4C. The apparatus 500 includes many of the same parts as the apparatus 300 of FIG. 3. A nonwoven web 512 is unwound from a roll 514 over a laminating roller 516 and directed to the melt curtain 304 while the melt curtain 304 is still molten at an impingement point 518 between the rotating forming structure 306 and the laminating roller 516. In an embodiment, the laminating roller 516 may be a point bond roller that includes a plurality of protrusions extending from a cylindrical surface of the roller 516.

The fibers of the nonwoven web 512 adjacent to the melt curtain 304 embed in the surface of the melt curtain 304 as the two layers cross over the vacuum slot 310 together, where the apertured protuberances are formed in the polymer web (i.e., the solidified melt curtain 304) in substantially the same pattern that is provided by the forming structure 306. As the polymer web (which solidifies to form, for example, the film layer 410 of FIG. 4C) is apertured, air flow is initiated through the apertured protuberances (e.g., 416) which cools and solidifies the apertured protuberances (e.g., 416). The polymer web is also cooled by the forming structure 306 as the fibers (e.g., 436) of the nonwoven are embedded in the land areas (e.g., 428) between the apertured protuberances (e.g., 416) so that the nonwoven is bonded to the film layer (e.g., 410) at the land areas (e.g., 428). The resulting vacuum formed film/nonwoven laminate 400 is pulled off of forming structure 306 by the peel roller 322 and travels to one or more subsequent rollers 324 until it may be wound by the winder 330 into a roll 532. Additional rollers and/or other pieces of equipment may be used in the apparatus 500.

The illustrated embodiment is not intended to be limiting in any way. For example, other lamination techniques may be used to create the film/nonwoven laminate 400. In an embodiment, the film layer may be manufactured using the apparatus 300 of FIG. 3 and later attached to a nonwoven web using known techniques, such as applying an adhesive to the film and/or nonwoven and then applying pressure to the two layers of materials, or using sonic or ultrasonic bonding techniques.

In an embodiment, either apparatus 300, 500 may also include additional equipment, such as intermeshing gears that may be used to activate the film 200 or the film/nonwoven laminate 400 in the machine direction or the transverse direction, if desired. Other equipment that may be included in the apparatus 300, 500 include, but are not limited to, corona treatment apparatus, printers, festooning equipment, spooling equipment, and additional processing equipment that may emboss or provide additional apertures to the film 200 or film/nonwoven laminate 400, as described in further detail below.

Figure 6:
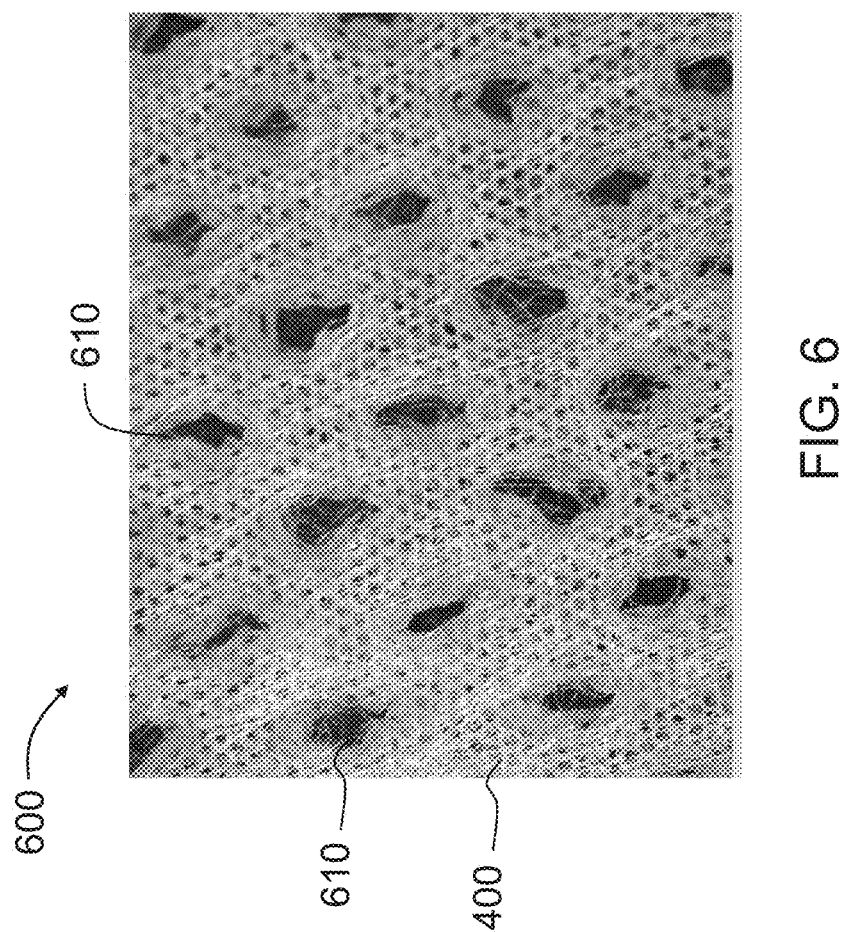
FIG. 6 is a microphotograph of one side of an apertured film/nonwoven laminate in accordance with an embodiment of the invention.

FIG. 6 illustrates and embodiment of a film/nonwoven laminate 600 that started as the film/nonwoven laminate 400 of FIGS. 4A-4C and then was further processed to form a plurality of macro apertures 610 in a pattern. The macro apertures 610 may be arranged in a pattern having between 3 apertures per linear inch and 40 apertures per linear inch (i.e., 3-40 mesh), desirably less than 20 apertures per linear inch (i.e. 20 mesh).

Figure 7:
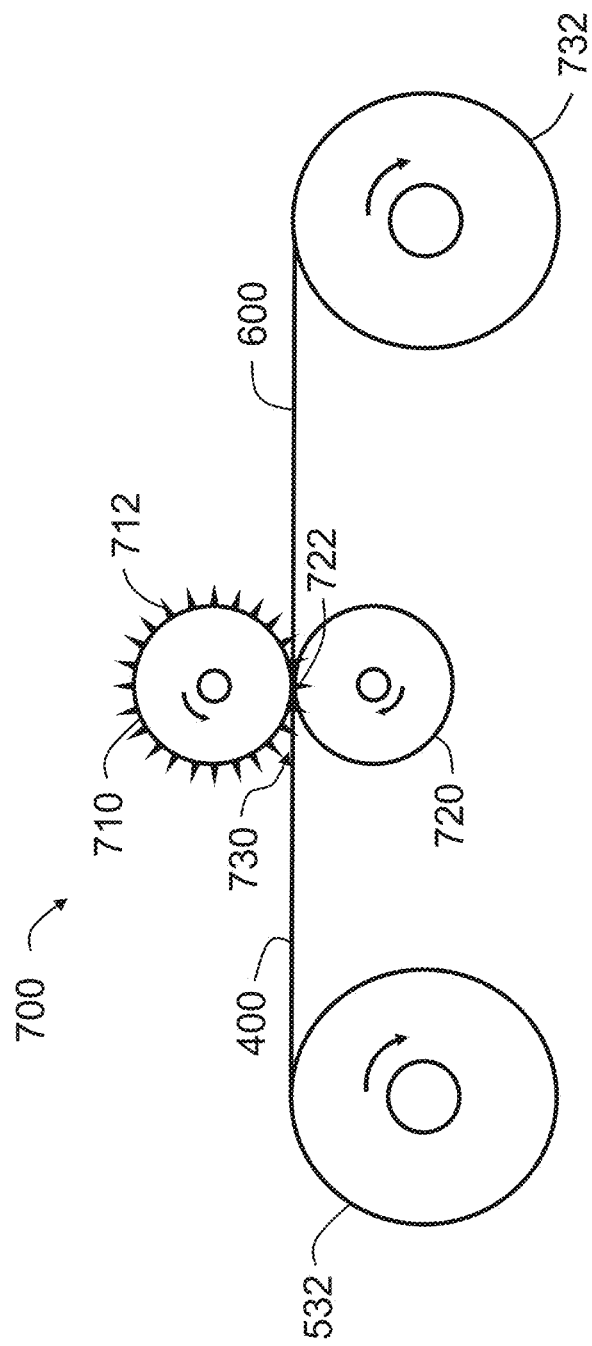
FIG. 7 is a schematic representation of an apparatus for manufacturing the apertured film/nonwoven laminate of FIG. 6.

FIG. 7 illustrates an apparatus 700 that may be used to create the macro apertures 610. As illustrated, the apparatus 700 includes a pin roll 710 having a pattern of pins 712 and a counter roll 720 having a matching pattern of cavities 722 configured to receive the pins 712. The pin roll 710 and the counter roll 720 may be rotated in opposite directions to form a nip 730 through which the film/nonwoven laminate 400 may be fed. The pins 712 protrude from the surface of pin roll 710 and the cavities 722 are recessed into the surface of the counter roll 710. The pin roll 710 and the counter roll 720 may be aligned so that when the pins 712 mate with the cavities 722 such that when the rolls 710, 720 are rotating, the pins 712 are inserted into the cavities 722 at the nip 730 and the laminate between the rolls 710, 720 is perforated by the pins 712, thereby forming the macro apertures 610. The resulting laminate 600 may be wound into a roll 732 for later conversion into, for example, a topsheet or other layer, in an absorbent article. In an embodiment, the apparatus 700 may be "in-line" with the apparatus of FIG. 5, such as between the roller 324 and the winder 330.

Figure 8B:
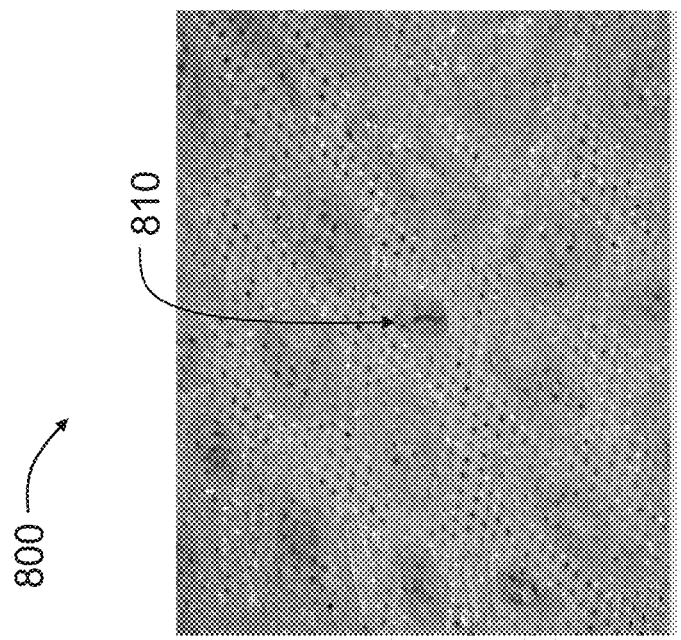
FIG. 8B is an enlarged microphotograph of an opposite side of the embossed film/nonwoven laminate of FIG. 8A.
Figure 8A:
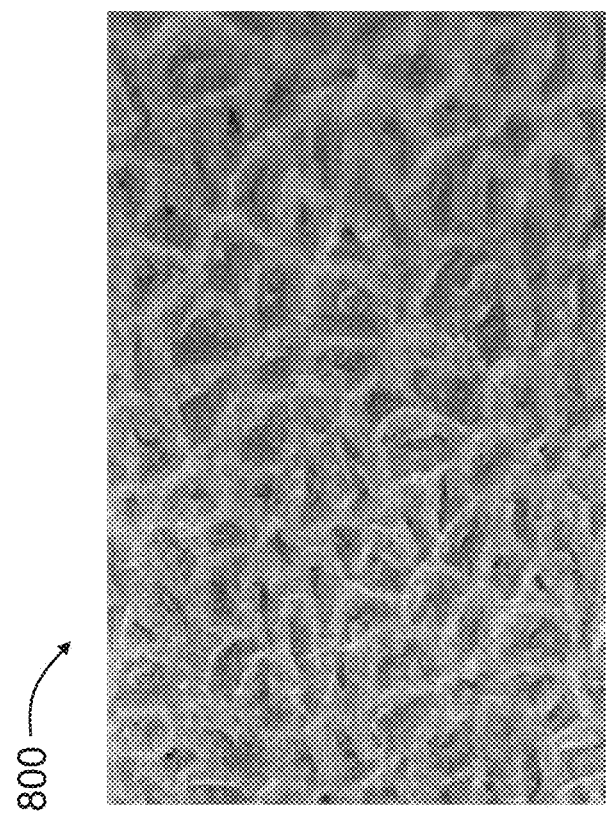
FIG. 8A is a microphotograph of one side of an embossed film/nonwoven laminate in accordance with an embodiment of the invention.

FIG. 8A is a photograph of an embodiment of an embossed laminate 800 that started as the film/nonwoven laminate 400 of FIGS. 4A-4C and was embossed with a pattern. As illustrated in FIG. 8B, macro apertures 810 may be formed in the pattern, although the illustrated embodiment is not intended to be limiting in any way. In an embodiment, the embossed laminate 800 only includes the plurality of microapertures that were formed in the original laminate before embossing. In an embodiment, additional macro apertures 810 may be formed in the film/nonwoven laminate 400 using the embossing process.

FIG. 9 illustrates and apparatus 900 that may be used to create the embossed laminate 800 of FIGS. 8A and 8B. As illustrated, the apparatus 900 includes matching embossing rolls 910, 920 that are configured to provide the pattern illustrated in FIGS. 8A and 8B. After the film/nonwoven laminate 400 passes between the embossing rolls 910, 920, the embossed laminate 800 may be rolled into a roll 932 for further processing. In embodiments in which it is desirable to form macro apertures, at least one of the embossing rolls 910, 920 may having suitable structures to pierce the laminate 400 and form the macro apertures 810. In an embodiment, the apparatus 900 may be "in-line" with the apparatus of FIG. 5, such as between the roller 324 and the winder 330.

Figure 10B:
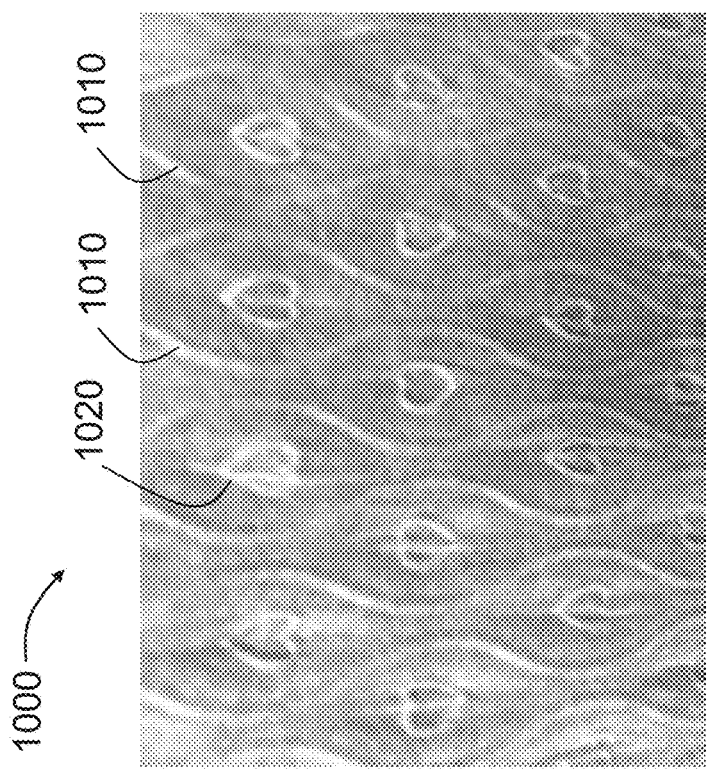
FIG. 10B is an enlarged photograph of the embossed film/nonwoven laminate of FIG. 10A.
Figure 10A:
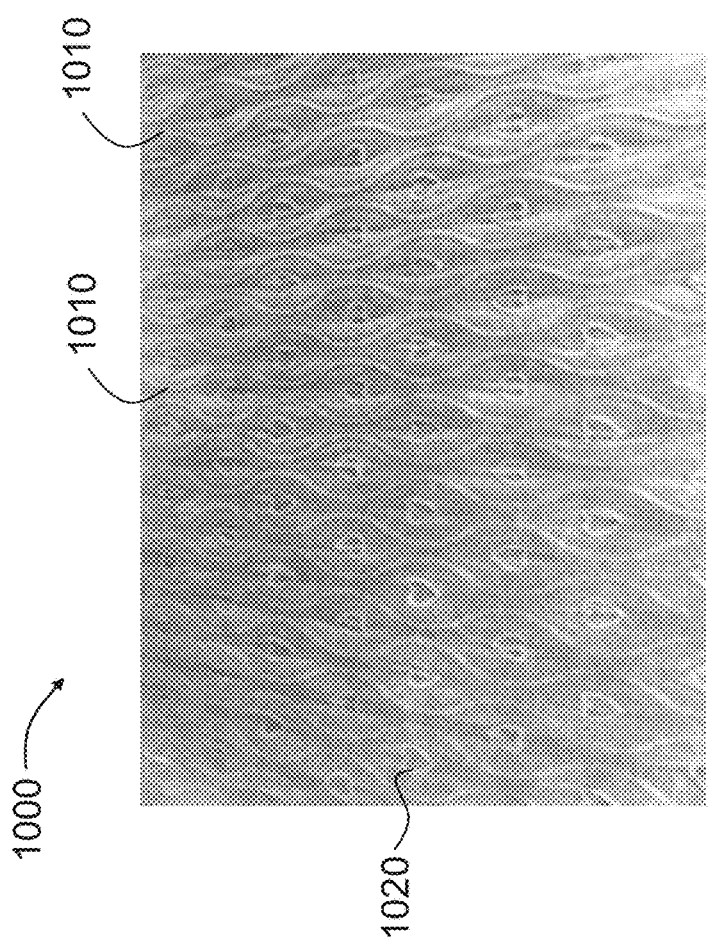
FIG. 10A is a photograph of one side of an embossed film/nonwoven laminate in accordance with an embodiment of the invention.

FIGS. 10A and 10B are photographs illustrating an embodiment of a film/nonwoven laminate 1000 that was made using the apparatus 500 illustrated in FIG. 5, and embossed with the apparatus of FIG. 9. In the illustrated embodiment, the nonwoven layer of the film/nonwoven laminate 1000 is the top layer and the film layer is beneath the nonwoven layer. The embossing rolls 910, 920 were designed to create a plurality of narrow, wavy ridges 1010 on one side of the film/nonwoven laminate 1000, as well as a plurality of narrow ridges that outline individual hearts 1020, as illustrated. Other shapes may be created in the film/nonwoven laminate 1000. The illustrated embodiment is not intended to be limiting in any way.

Figure 11:
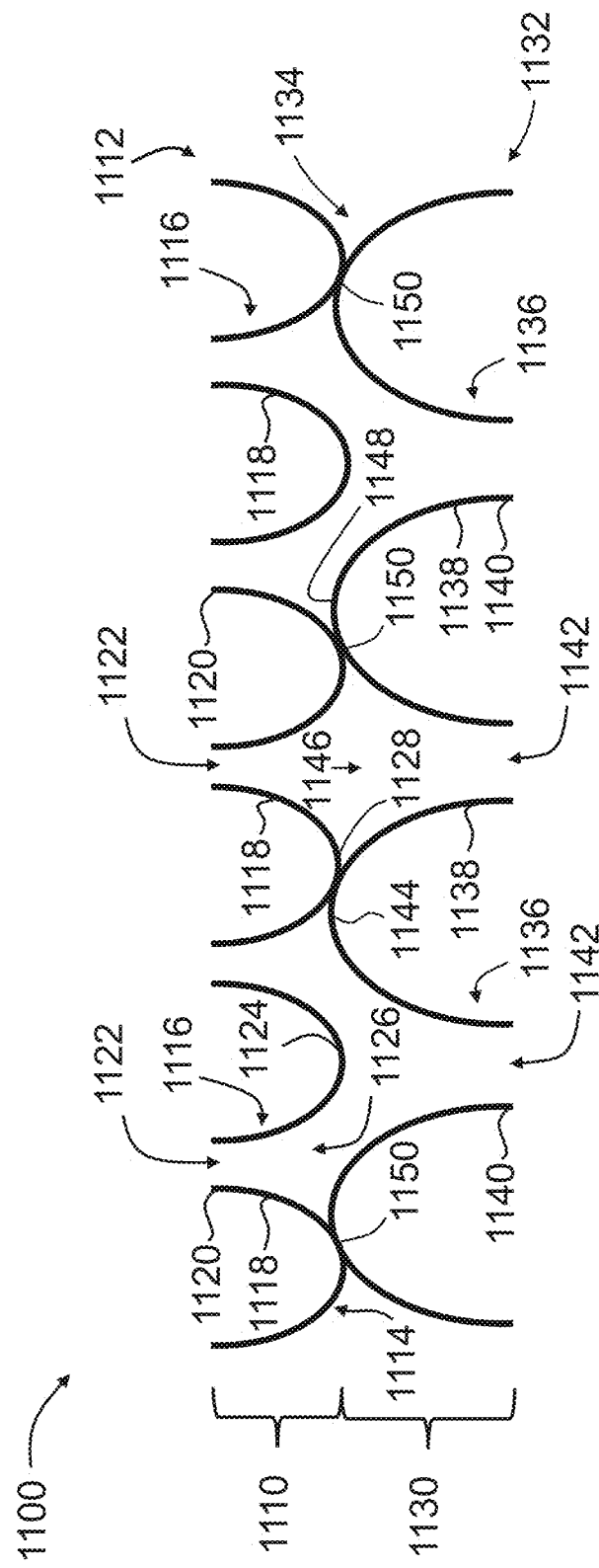
FIG. 11 is a schematic enlarged cross-section of a film/film laminate in accordance with an embodiment of the invention that may be used in the absorbent article of FIG. 1.

FIG. 11 schematically illustrates a cross-section of a portion of a film/film laminate 1100, which may be used as the topsheet 110 for the absorbent article 100 of FIG. 1, or as a combination of the topsheet 110 and fluid distribution material 140 for the absorbent article 100 of FIG. 1. As illustrated in FIG. 11, the film/film laminate 1100 includes a first film layer 1110 attached to a second film layer 1130. The first film layer 1110 has a first side 1112 and a second side 1114 that is opposite the first side 1112. The first film layer 1110 includes a plurality of apertured protuberances 1116. Each of the apertured protuberances 1116 includes a continuous sidewall 1118 extending from the first side 1112 of the first film layer 1110 to a distal end 1120 that includes a secondary aperture 1122, as illustrated. The first side 1112 of the first film layer 1110 also includes land areas 1124 in between the apertured protuberances 1116.

The second side 1114 of the first film layer 1110 has a plurality of primary apertures 1126 aligned with the plurality of protuberances 1116. As such, the primary apertures 1126 in the second side 1114 of the first film layer 1110 are also considered to be proximal apertures 1126 of the apertured protuberances 1116, while the secondary apertures 1122 at the distal ends 1120 of the apertured protuberances 1116 may also be considered to be distal apertures 1122 of the apertured protuberances 1116. The second side 1114 of the first film layer 1110 also includes land areas 1128 in between the proximal apertures 1126. The first film layer 1110 may include one or more of the polymers listed about with respect to the film 200, and may have a basis weight between about 4 gsm and about 20 gsm.

In an embodiment, the apertured protuberances 1116 may be arranged in a pattern having about 60 to about 120 protuberances per linear inch or "mesh," i.e., about 60 mesh to about 120 mesh in at least one direction (e.g., in the machine direction of the film/film laminate 1100 and/or the transverse direction of the film/film laminate 1100, which is orthogonal to the machine direction). The pattern may be a hexagonal pattern, a square pattern, a staggered pattern, or any other type of pattern or design. In an embodiment, the proximal apertures 1126 may be hexagonal in shape and have approximately the same size.

The second film layer 1130 has a first side 1132 and a second side 1134 that is opposite the first side 1132. The second film layer 1130 includes a plurality of apertured protuberances 1136. Each of the apertured protuberances 1136 includes a continuous sidewall 1138 extending from the first side 1132 of the second film layer 1130 to a distal end 1140 that includes a secondary aperture 1142, as illustrated. The first side 1132 of the second film layer 1130 also includes land areas 1144 in between the apertured protuberances 1136.

The second side 1134 of the second film layer 1130 has a plurality of primary apertures 1146 aligned with the plurality of protuberances 1136. As such, the primary apertures 1146 in the second side 1134 of the second film layer 1130 are also considered to be proximal apertures 1146 of the apertured protuberances 1136, while the secondary apertures 1142 at the distal ends 1140 of the apertured protuberances 1136 may also be considered to be distal apertures 1142 of the apertured protuberances 1136. The second side 1134 of the second film layer 1130 also includes land areas 1148 in between the proximal apertures 1146. The second film layer 1130 may include one or more of the polymers listed about with respect to the film 200, and may have a basis weight between about 10 gsm and about 40 gsm.

In an embodiment, the apertured protuberances 1136 may be arranged in a pattern having about 3 to about 40 protuberances per linear inch or "mesh," i.e., about 3 mesh to about 40 mesh in at least one direction (e.g., in the machine direction of the film/film laminate 1100 and/or the transverse direction of the film/film laminate 1100, which is orthogonal to the machine direction). The pattern may be a hexagonal pattern, a square pattern, a staggered pattern, or any other type of pattern or design. In an embodiment, the proximal apertures 1146 may be hexagonal in shape and have approximately the same size.

The first film layer 1110 is attached to the second film layer 1130 at bond sites 1150 where the land areas 1148 of the second side 1134 of the second film layer 1130 contact the land areas 1128 of the second side 1114 of the first film layer 1110. In an embodiment, the first film layer 1110 and the second film layer 1130 may be attached by a vacuum formed lamination process, as described in further detail below.

Figure 12:
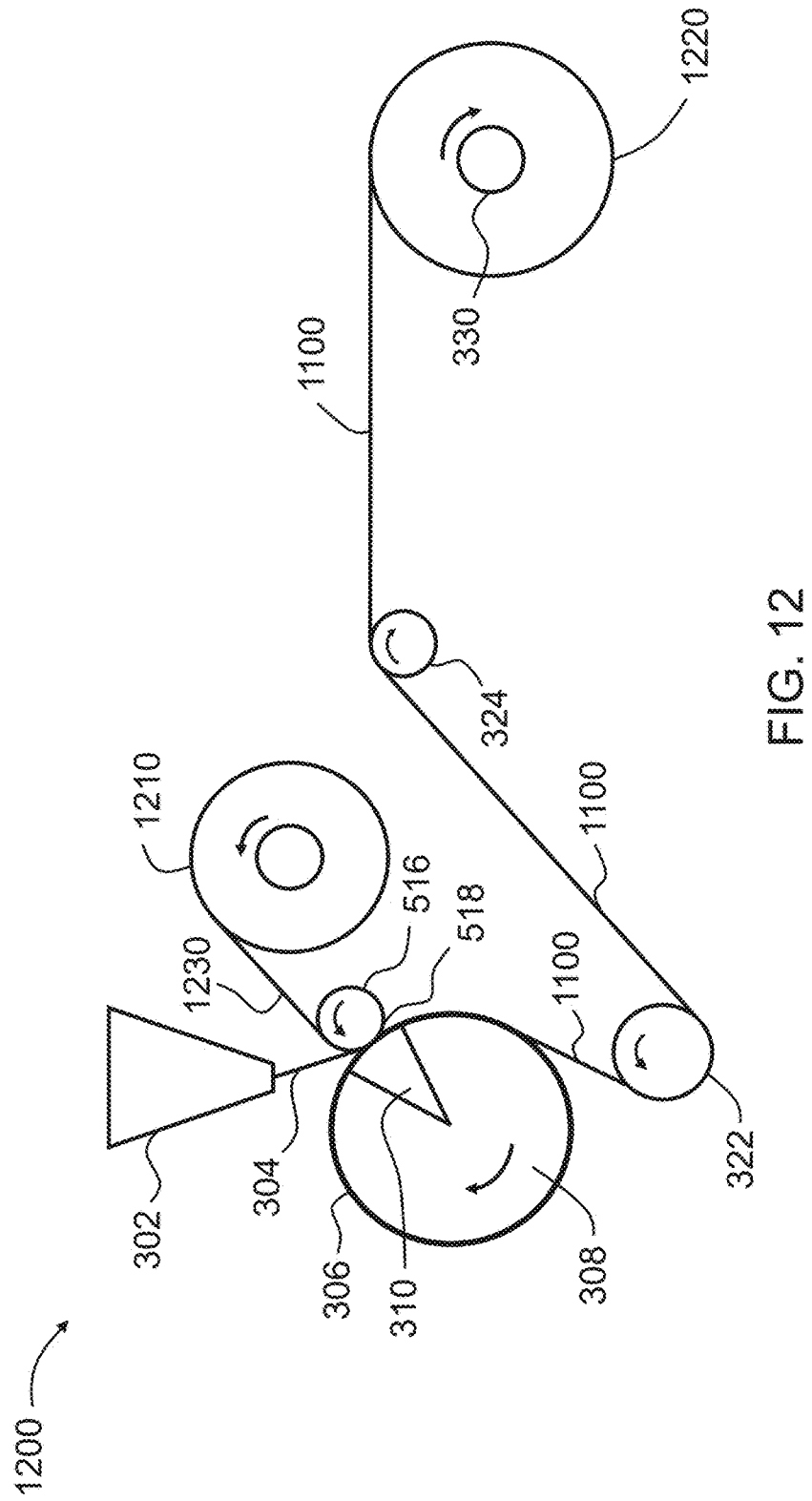
FIG. 12 is schematic representation of an apparatus for manufacturing the film/film laminate of FIG. 11.

FIG. 12 illustrates an embodiment of an apparatus 1200 that may be used to manufacture the film/film laminate 1100 of FIG. 11. The apparatus 1200 includes many of the same parts as the apparatus 500 of FIG. 5. An apertured film 1230, which is to become the second film layer 1130 of the film/film laminate 1100, is unwound from a roll 1210 over the laminating roller 516 and directed to the melt curtain 304 while the melt curtain 304 is still molten at the impingement point 518 between the rotating forming structure 306 and the laminating roller 516.

The side of the apertured film 1230 adjacent to the melt curtain 304, which coincides with the second side 1134 of the second film layer 1130, contacts the surface of the melt curtain 304 as the two layers cross over the vacuum slot 310 together, where the apertured protuberances are formed in the polymer web (i.e., the solidified melt curtain 304) in substantially the same pattern that is provided by the forming structure 306. As the polymer web (which solidifies to form, for example, the first film layer 1110 of FIG. 11) is apertured, air flow is initiated through the apertured protuberances (e.g., 1116) which cools and solidifies the apertured protuberances (e.g., 1116). The polymer web is also cooled by the forming structure 306 as the land areas (e.g., 1148) of the apertured film 1130 bond to the land areas (e.g., 1128) between the apertured protuberances (e.g., 1116) so that the apertured film 1230 is bonded to the first film layer (e.g., 1110) at the land areas (e.g., 1128). The resulting vacuum formed film/film laminate 1100 is pulled off of the forming structure 306 by the peel roller 322 and travels to one or more subsequent rollers 324 until it may be wound by the winder 330 into a roll 1220. Additional rollers and/or pieces of equipment may be used in the apparatus 1100.

The illustrated embodiment is not intended to be limiting in any way. For example, other lamination techniques may be used to create the laminate 1100. In an embodiment, the first film layer 1110 and the second film layer 1130 may be manufactured separately using the apparatus 300 of FIG. 3 and later attached to each other known techniques, such as applying an adhesive to the one of the film layers 1110, 1130 and then applying pressure to the two film layers 1110, 1130, or using sonic or ultrasonic bonding techniques. In an embodiment, the first film layer 1110 may be made first and then vacuum laminated to the second film layer 1130 as the second film layer 1130 is vacuum formed (i.e., the reverse of what is illustrated in FIG. 12).

In an embodiment, the apparatus 1200 may also include additional equipment, such as intermeshing gears that may be used to activate the film/film laminate 1100 in the machine direction or the transverse direction, if desired. Other equipment that may be included in the apparatus 1200 include, but are not limited to, corona treatment apparatus, printers, festooning equipment, spooling equipment, and additional processing equipment that may emboss or provide additional apertures to the film/film laminate 1100, as described above.

The embodiments described herein represent a number of possible implementations and examples and are not intended to necessarily limit the present disclosure to any specific embodiments. Instead, various modifications can be made to these embodiments, and different combinations of various embodiments described herein may be used as part of the invention, even if not expressly described, as would be understood by one of ordinary skill in the art. Any such modifications are intended to be included within the spirit and scope of the present disclosure and protected by the following claims.

What is claimed is:

1. A film for use in an absorbent article, the film comprising:
   a first side and a second side opposite the first side,
   a plurality of apertured protuberances arranged in a pattern having 60 to 120 protuberances per linear inch in at least one direction, each of the protuberances comprising a continuous sidewall extending from the first side, the second side having a plurality of apertures aligned with the plurality of apertured protuberances and land areas in between the apertures,
   wherein the film has a melt index of at least about 8 g/10 min and an air permeability of at least about 80 $m^3/m^2/min$ to 204.4 $m^3/m^2/min$.

2. The film according to claim 1, wherein the film has a basis weight between about 10 gsm and about 30 gsm.

3. A laminate for use in an absorbent article, the laminate comprising
   a film layer having a first side and a second side opposite the first side, the film layer comprising a plurality of apertured protuberances arranged in a pattern having 60 to 120 protuberances per linear inch in at least one direction, each of the protuberances comprising a continuous sidewall extending from the first side, the second side having a plurality of apertures aligned with the plurality of apertured protuberances and land areas in between the apertures, wherein the film layer has a melt index of at least about 8 g/10 min and an air permeability of at least about 80 $m^3/m^2/min$ to 204.4 $m^3/m^2/min$; and
   a nonwoven layer laminated to the second side of the film layer, the nonwoven layer comprising a plurality of fibers attached to the formed film at the land areas of the film layer.

4. The laminate according to claim 3, wherein the nonwoven layer has a basis weight of between about 8 gsm and about 60 gsm.

5. The laminate according to claim 3, wherein the nonwoven layer comprises a spunbond nonwoven.

6. The laminate according to claim 3, wherein the nonwoven layer comprises a carded nonwoven.

7. The laminate according to claim 3, wherein the nonwoven layer comprises a spunlace nonwoven.

8. The laminate according to claim 3, wherein the film layer has a basis weight of between about 4 gsm and about 20 gsm.

9. The laminate according to claim 3, further comprising a plurality of apertures extending through the film layer and the nonwoven layer, the plurality of apertures having a pattern with a mesh count between about 3 and about 40 apertures per linear inch in at least one direction.

10. The laminate according to claim 3, wherein the laminate has an embossed pattern.

11. The laminate according to claim 10, wherein the embossed pattern comprises a plurality of narrow ridges.

12. The laminate according to claim 11, wherein the plurality of narrow ridges includes narrow, wavy ridges.

13. A laminate for use in an absorbent article, the laminate comprising:
   a first film layer having a first side and a second side opposite the first side, the first film layer comprising a first plurality of apertured protuberances arranged in a pattern having 60 to 120 protuberances per linear inch in at least one direction, each of the first plurality of apertured protuberances comprising a continuous sidewall extending from the first side, the second side having a first plurality of apertures aligned with the first plurality of apertured protuberances and first land areas in between each of the first plurality of apertures, wherein the first film layer has a melt index of at least about 8 g/10 min and an air permeability of at least about 80 $m^3/m^2/min$; and
   a second film layer having a first side and a second side opposite the first side, the second film layer comprising a second plurality of apertured protuberances arranged in a pattern having 3 to 40 protuberances per linear inch in at least one direction, each of the second plurality of apertured protuberances comprising a continuous sidewall extending from the first side, the second side having a second plurality of apertures aligned with the second plurality of apertured protuberances and second land areas in between each of the second plurality of apertures, wherein the second side of the first film layer is attached to the second side of the second film layer.

14. The laminate according to claim 13, the first film layer has a basis weight of between about 4 gsm and about 20 gsm.

15. The laminate according to claim 13, wherein the second film layer has a basis weight of between about 10 gsm and about 40 gsm.

16. A method for making a material for an absorbent article, the method comprising:

vacuum forming a plurality of apertured protuberances into a polymer web to create a first film using a forming structure comprising a pattern of 60 to 120 apertures per linear inch in at least one direction, wherein the first film has a melt index of at least about 8 g/10 min and an air porosity of at least about 80 $m^3/m^2$/min to 204.4 $m^3/m^2$/min.

17. The method according to claim 16, further comprising laminating a nonwoven to the first film to form a film/nonwoven laminate.

18. The method according to claim 17, further comprising aperturing the film/nonwoven laminate to create a plurality of apertures having a mesh count between about 3 to about 40 apertures per linear inch in at least one direction.

19. The method according to claim 17, further comprising embossing the film/nonwoven laminate to create an embossed pattern in the film/nonwoven laminate.

20. The method according to claim 19, wherein the embossed patterned includes a plurality of narrow ridges.

21. The method according to claim 20, wherein the plurality of narrow ridges includes narrow, wavy ridges.

22. The method according to claim 16, further comprising laminating a second film to the first film to form a film/film laminate.

23. The method according to claim 22, wherein the second film comprises a plurality of apertures arranged in a pattern of 3 to 40 apertures per linear inch in at least one direction.

* * * * *